(12) United States Patent
Harlin et al.

(10) Patent No.: US 8,952,194 B2
(45) Date of Patent: Feb. 10, 2015

(54) HYDROGEN TREATMENT OF IMPURE TALL OIL FOR THE PRODUCTION OF AROMATIC MONOMERS

(75) Inventors: Ali Harlin, Espoo (FI); Jari Räsänen, Imatra (FI); Tapani Penttinen, Huutjärvi (FI)

(73) Assignee: Stora Enso OYJ, Helsinki (FI)

( * ) Notice: Subject to any disclaimer, the term of this patent is extended or adjusted under 35 U.S.C. 154(b) by 107 days.

(21) Appl. No.: 13/701,664

(22) PCT Filed: Jun. 3, 2011

(86) PCT No.: PCT/FI2011/050520
§ 371 (c)(1),
(2), (4) Date: Feb. 18, 2013

(87) PCT Pub. No.: WO2011/151528
PCT Pub. Date: Dec. 8, 2011

(65) Prior Publication Data
US 2013/0178650 A1 Jul. 11, 2013

(30) Foreign Application Priority Data

Jun. 3, 2010 (FI) .................................. 20105628
Jul. 28, 2010 (FI) .................................. 20105829

(51) Int. Cl.
*C07C 51/16* (2006.01)
*C07C 51/255* (2006.01)
(Continued)

(52) U.S. Cl.
CPC ................ *C10G 3/50* (2013.01); *C07C 51/265* (2013.01); *C10G 3/49* (2013.01); *C07C 1/2078* (2013.01);
(Continued)

(58) Field of Classification Search
None
See application file for complete search history.

(56) References Cited

U.S. PATENT DOCUMENTS 2,863,914 A   12/1958 Raecke
2,891,992 A   6/1959 Raecke et al.
(Continued)

FOREIGN PATENT DOCUMENTS

DE       936 036          12/1955
DE       195 21 222 A1    12/1996
(Continued)

OTHER PUBLICATIONS

Internet: Wikipedia/Naphtha, hhttp://en.wikipedia.org/w/index.php?title=Naphth&oldid=363432035, julk, May 21, 2010, 5 pages.
(Continued)

*Primary Examiner* — Rosalynd Keys
*Assistant Examiner* — Jennifer C Sawyer
(74) *Attorney, Agent, or Firm* — Patterson Thuente Pedersen, P.A.

(57) ABSTRACT

A method of manufacturing aromatic hydrocarbons, which are suitable for the production of terephthalic acid, from tall oil-based raw material. According to the invention, the raw material that contains tall oil or its fraction is catalytically deoxygenated with hydrogen, and one or more aromatic hydrocarbons that can be converted into terephthalic acid are separated from the deoxygenated reaction yield. The deoxygenation catalyst is a NiMo catalyst and, in addition, a cracking catalyst can be used, such as an acidic zeolite catalyst. The separated hydrocarbon can be p-xylene, o-xylene or p-cymene. According to the invention, these can be converted by oxidation and, when needed, by a re-arrangement reaction into terephthalic acid that is suitable for the source material of the manufacture of bio-based polyethylene terephthalate.

19 Claims, 1 Drawing Sheet

(51) Int. Cl.
*C07C 51/265* (2006.01)
*C10G 3/00* (2006.01)
*C07C 1/207* (2006.01)

(52) U.S. Cl.
CPC ............. *C07C 51/16* (2013.01); *C07C 2521/04* (2013.01); *C07C 2523/883* (2013.01); *C10G 3/46* (2013.01); *C10G 2400/30* (2013.01); *C10G 2300/1014* (2013.01)
USPC ........................................................ 562/409

(56) References Cited

U.S. PATENT DOCUMENTS

| | | | |
|---|---|---|---|
| 3,312,635 | A | 4/1967 | Liquori |
| 4,300,009 | A | 11/1981 | Haag et al. |
| 5,705,722 | A | 1/1998 | Monnier et al. |
| 2004/0230085 | A1 | 11/2004 | Jakkula et al. |
| 2007/0131579 | A1 | 6/2007 | Koivusalmi et al. |
| 2007/0135669 | A1 | 6/2007 | Koivusalmi et al. |
| 2008/0154073 | A1 | 6/2008 | Petri et al. |
| 2008/0161620 | A1 | 7/2008 | Bozzano et al. |
| 2008/0308457 | A1 | 12/2008 | Dindi et al. |

FOREIGN PATENT DOCUMENTS

| | | |
|---|---|---|
| EP | 1 194 236 B1 | 11/2003 |
| EP | 2 003 159 A1 | 12/2008 |
| GB | 2 398 073 A1 | 8/2004 |
| WO | WO 99/10450 | 3/1999 |
| WO | WO 2007/133973 A2 | 11/2007 |
| WO | WO 2008/027699 A2 | 3/2008 |
| WO | WO 2008/067112 A2 | 6/2008 |
| WO | WO 2008/101945 A1 | 8/2008 |
| WO | WO 2009/004181 A2 | 1/2009 |
| WO | WO 2009/120457 A2 | 10/2009 |
| WO | WO 2010/028717 A2 | 3/2010 |
| WO | WO 2010/028717 A3 | 3/2010 |
| WO | WO 2010/086507 A1 | 8/2010 |

OTHER PUBLICATIONS

B. Holmbom, "Composition of Tall Oil Pitch", Journal of the American Oil Chemists' Society, vol. 55, Mar. 1978, pp. 342-345.

Lars-Hugo Norlin et al., "Tall Oil", 2005 Wiley-VCH Verlag GmbH & Co., KGaA, Weinheim, pp. 1-14, Sandarne, Sweden.

C.E. Senseman et al., "Catalytic Oxidation of *p*-Cymene in the Vapor Phase", Bureau of Chemistry and Soils, U.S. Department of Agriculture, Washington, D.C., Industrial and Engineering Chemistry, Oct. 1931, pp. 1129-1131.

Supplementary Partial European Search Report for EP Application 11789319.8, dated Jun. 17, 2014.

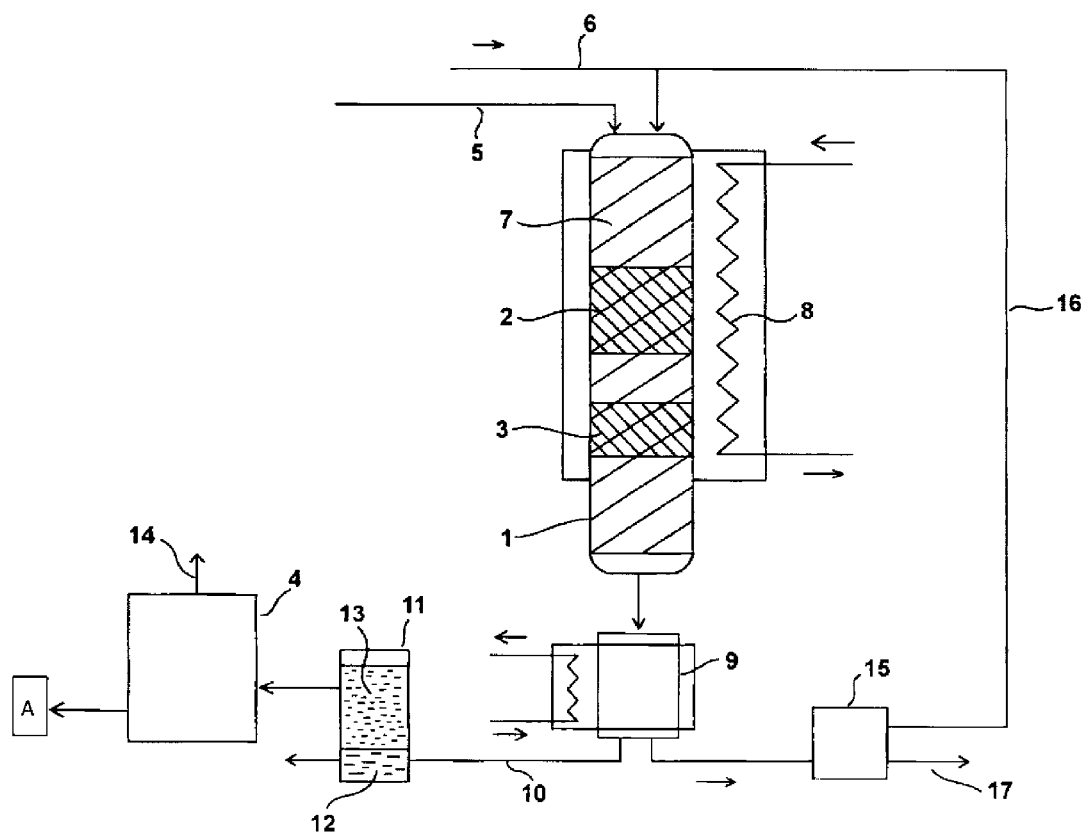

US 8,952,194 B2

HYDROGEN TREATMENT OF IMPURE TALL OIL FOR THE PRODUCTION OF AROMATIC MONOMERS

PRIORITY CLAIM

This application is a National Phase entry of PCT Application No. PCT/FI2011/050520, filed Jun. 3, 2011, which claims priority from Finland Application No. 20105628 filed Jun. 3, 2010, and Finland Application No. 20105829, filed Jul. 28, 2010, the disclosures of which are hereby incorporated by referenced herein in their entirety.

FIELD OF THE INVENTION

The invention relates to a method of manufacturing aromatic hydrocarbons suitable for the production of terephthalic acid from tall oil-based raw material. The invention also relates to a method of manufacturing bio-based terephthalic acid.

BACKGROUND OF THE INVENTION

According to present practice, terephthalic acid is manufactured from p-xylene by oxidation, in particular. Other forms of xylene (meta and ortho) can be converted to be suitable, for example, by the Henkel reaction or its modification. The Henkel reaction is an industrial-scale process, wherein the alkali salts of aromatic acids are re-arranged using a thermal reaction in the presence of a metallic salt, such as cadmium salt (see, for example, DE 936036).

Terephthalic acid is mainly used as the precursor of polyethylene terephthalate (PET) and polybutylene terephthalate (PBT). PET is used, among others, for the manufacture of fibers for the clothing industry, the manufacture of plastic containers, such as plastic bottles, and for polymeric coating of paper or board in the packaging industry. In the manufacture of PET, generally, a catalyzed process is used, where an aromatic acid and an aliphatic diol are made to react together in the catalyzed process, wherein the catalyst contains, for example, titanium (among others, EP 2 003 159) or antimony (among others, GB 2 398 073).

Bio-based raw materials that are suitable for the manufacture of PET, for example, can be found on the market to an increasing extent, but a central problem when manufacturing this bio-based PET, however, is to find a uniform bio mass-based raw material suitable for the purpose; for example, for the manufacture of terephthalic acid, which is used in the manufacture of PET, by an industrial-scale process. The aliphatic portion of such corresponding polyesters, that is, the diol mentioned above, is already available from bio-based sources, but it is more difficult to find the source of a suitable aromatic part.

The conventional raw material for the manufacture of aromatic monomers has comprised crude oil. The aromatic fractions obtained from the fractional distillation of crude oil have been further processed to obtain aromatic monomers, unsubstituted or substituted, such as benzene, xylene and phenol. In addition to the aromatic fractions, aliphatic fractions are recovered from the source material and used as the raw material of polymers, among others.

As a substitutive alternative for fossil raw materials, sources of renewable organic raw materials have been explored for the manufacture of polymers. An ideal source of raw material for the aromatic monomers suitable for the manufacture of terephthalic acid would comprise wood that has abundant reserves; the by-products of the manufacturing process of chemical pulp, such as tall oil, in particular.

The specification of US-2004/0230085 discloses the catalytic hydrodeoxygenation of tall oil fatty acids as part of the manufacture of a diesel fuel of biological origin. The deoxygenation is carried out by gaseous hydrogen in a catalyst bed, where there is a metallic catalyst, such as NiMo or CoMo, and the carrier comprises alumina and/or silica. From the gas mixture created at the deoxygenation stage, oxides of carbon and various impurities are separated, and the purified hydrogen is circulated back to the process. At the second stage of the process, isomerization is carried out for the liquid phase, converting the product into a form suitable for use as fuel. Since the isomerization stage is sensitive to aromatic and naphthene impurities, tall oil resin acids, from which they can be formed in the deoxygenation, are removed from the source material as effectively as possible. In the example 1 of the specification, there were 1.9% of resin acids among the fatty acids.

The specification of US-2008/0154073 discloses a similar process for the manufacture of diesel fuel from biorenewable raw materials, such as vegetable oils. As a potential raw material, tall oil is mentioned, comprising resin acids in addition to fatty acids, but according to test results, tall oil produced a considerable portion of hydrocarbon fractions heavier than diesel, unlike the soybean oil that was also used in the tests.

The specification of US-2007/0135669 also describes the manufacture of diesel fuel from biorenewable raw materials and observes the unwanted presence of unsaturated and aromatic hydrocarbons in the end product. The specification discloses the invention of a process, wherein the fatty acids distilled from tall oil are first isomerized and thereafter, at the second stage of the process, deoxygenated.

The specification of WO-2009/004181 A2 discloses the catalytic hydrocracking of vegetable oils and the subsequent steam cracking into monomers suitable for polymerization. The vegetable oils mentioned in the specification do not contain resin acids of tall oil.

The specification of U.S. Pat. No. 5,705,722 A discloses the catalytic hydrocracking of a mixture of tall oil fatty and resin acids and the use of the obtained product as additives of diesel fuel. The publication, however, does not disclose the recovery of aromates.

SUMMARY OF THE INVENTION

The problem to be solved by embodiments of the invention is, thus, to find an industrially suitable process, by which raw material that is based on wood can be converted into monoaromates suitable for the manufacture of terephthalic acid and, therefrom, further into terephthalic acid. The manufacture of monoaromates, similarly to that of terephthalic acid, is thus based on renewable biological sources of raw material. When polymerized with a bio-based glycol, a purely bio-based PET can be further produced from terephthalic acid. The solution is the method of manufacturing monoaromates, according to the invention, wherein:
  raw material that contains tall oil or its fraction is brought into contact with hydrogen and one or more catalysts;
  the raw material is catalytically deoxygenated with hydrogen; and
  one or more aromatic hydrocarbons (A) that can be converted into terephthalic acid are separated from the deoxygenated reaction yield (10).

The oil source material can be purely tall oil-based, consisting of tall oil fatty acids and of at least 2%, and more particularly, at least 25% of tall oil resin acids. The composition of crude tall oil corresponds to these values, but advantageous acid mixtures can also be separated from crude tall oil by distillation.

It is also possible to blend the tall oil components in the source material with other suitable bio oils, such as vegetable oils, for example, palm oil.

The tall oil in the invention refers to an oil product, which is obtained not only from pine (pinus) but also from other softwood trees and which consists of fatty and resin acids or their esters.

The resin acid fraction of tall oil consists of acids of the abietic acid type (85-90% of typical tall oil) and acids of the pimaric acid type (10-15% of typical tall oil), in particular. These resin acids include abietic acid, dehydroabietc acid, isopimaric acid, neoabietic acid, palustric acid, pimaric acid, and sandaracopimaric acid which, through deoxygenation and degradation, form monoaromates, among which there is a considerable portion of source materials that are suitable for the manufacture of terephthalic acid.

Surprisingly, the inventors of the present invention have observed that when using, in the method, a suitable deoxygenation catalyst, monoaromates, such as benzene, toluene, and xylene can be formed with crude tall oil (CTO), distilled tall oil (DTO) that is slightly fractioned, and tall oil fatty acids (TOFA) in connection with the hydrogen treatment. The monoaromates, such as p-xylene, m-xylene, o-xylene, or p-cymene, which are suitable for the manufacture of terephthalic acid, can be separated from the liquid phase of the reaction yield of the catalyst stage by fractional distillation, for example.

The separation and further processing of monoaromates is a technique that pertains to normal petrochemistry; therefore, it is easy to implement the process according to the invention, in practice.

An embodiment of the method according to the invention includes:
  hydrogen gas and bio oil containing 2-90% of tall oil fatty acids and 2-98% of tall oil resin acids, are fed into a fixed catalyst bed (7);
  bio oil is catalytically deoxygenated in the bed (7) with hydrogen;
  the flow exiting the bed (7) is cooled and divided into a hydrocarbon-bearing liquid phase (10) and a gas phase; and
  one or more aromatic hydrocarbons (A) are recovered from the hydrocarbon-bearing liquid phase.

In the invention, a catalyst can be used that comprises a NiMo catalyst or, optionally, a combination of catalysts that comprises the NiMo catalyst and a ZSM-5 catalyst. As an unexpected feature and advantage, the inventors observed that when using these catalysts (NiMo, ZSM-5 and their combinations), no polycycles or deposits were created in the catalyst. Thus, they were more advantageous than the acidic montmorolite, which is used as a catalyst and which disturbs the process.

The catalytic hydrodeoxygenation works by releasing oxygen from fatty acids and forming water, carbon monoxide and/or carbon dioxide. No significant breaking of carbon chains into smaller molecules happens yet, which is advantageous for the recovery of aromates. In the invention, the exploitation of the catalytic fixed bed can be limited to the deoxygenation stage.

An alternative application of the invention is that the deoxygenation is followed by catalytic cracking in the fixed bed to reduce molar mass, whereby the catalysts of the deoxygenation and cracking stages are different from each other and located apart from each other in the bed. Cracking creates unsaturated hydrocarbons and releases hydrogen, so that the hydrogen-bearing gas exiting them can be circulated back to the deoxygenation stage. In that case, it is even possible that the process requires an external source of hydrogen at the initiation stage only, and simply works thereafter by the circulated hydrogen.

As the catalyst of the cracking in the fixed bed, acidic catalysts can be used, such as an acidic zeolite catalyst or montmorolite catalyst. As the catalyst of the deoxygenation stage, regardless of the possible catalytic cracking, a metallic catalyst, such as NiMo or CoMo, can be used. The latter are reduced with hydrogen and treated with hydrogen sulfide in a well-known manner. In the method according to a non-limiting embodiment of the invention, the NiMo catalyst is preferable, because it produces aromates from the CTO feed with a high yield, but is not sensitive to coking.

In a particular embodiment, the catalyst of the cracking stage is acidic, such as the acidic zeolite catalyst, and particularly the ZSM-5 catalyst.

By the means of suitable catalysts, hydrodeoxygenation and considerable catalytic cracking can take place in the bed simultaneously. Such catalysts include nickel-bearing Y zeolite (NiY zeolite) or nickel-bearing montmorolite (NiSMM), which require a high hydrogen pressure in the reactor. NiSMM also cracks resin acids and is, thus, particularly advantageous for the effective exploitation of the tall oil components.

A suitable reaction temperature at the hydrodeoxygenation and possible catalytic cracking stages is within 330-450° C. At lower temperatures, there is a risk of polymerization, at higher temperatures, coking; already when feeding the fatty acids into the reactor. To avoid coking, a temperature is within 330-400° C. A suitable pressure at the hydrodeoxygenation and cracking stages is 50-100 bars. The processing can be continued for 30-60 minutes, and more particularly 35-50 minutes.

In the method of manufacturing bio-based terephthalic acid, according to the invention:
  raw material that contains tall oil or its fraction is brought into contact with hydrogen and one or more catalysts;
  the raw material is catalytically deoxygenated with hydrogen;
  aromatic hydrocarbon that can be converted into terephthalic acid is separated from the obtained reaction yield as an intermediate product; and
  oxygenation and a possible rearrangement reaction are carried out for the separated hydrocarbon, so that terephthalic acid is obtained as an end product.

According to a particular embodiment, the method according to the invention is carried out by catalytically converting the raw material by separating a suitable xylene isomer from the liquid phase of the reaction yield, for example, by distillation, and by carrying out the stages subsequent to the separation, according to formula 1:

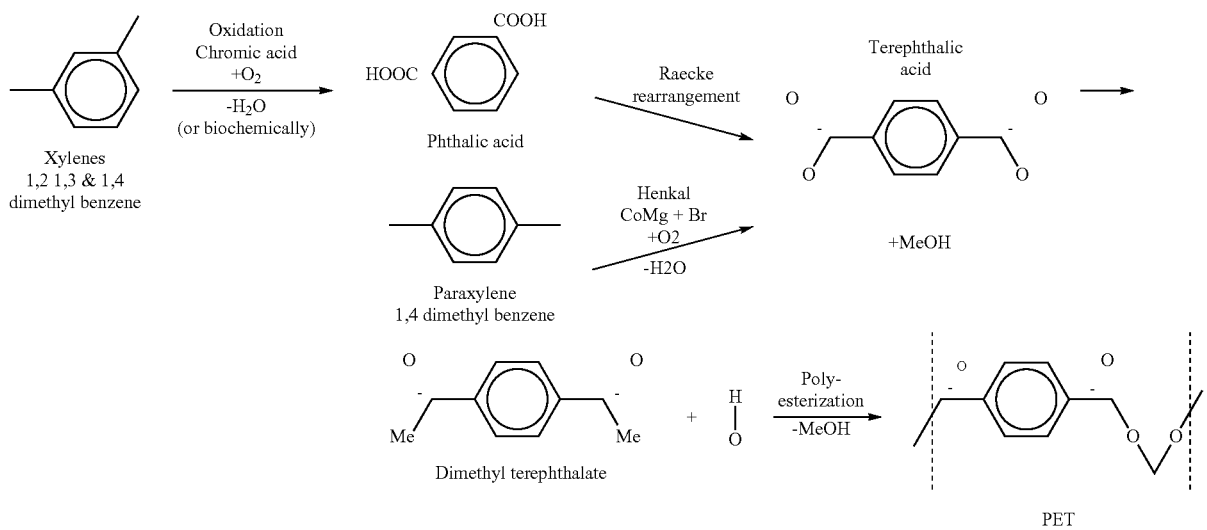

Formula 1

The oxidation can be carried out with a suitable chemical or biochemical oxidizer, and particularly chromic acid. Depending on the selected xylene isomer, phthalic acid or terephthalic acid is obtained as a result of the oxidation.

The phthalic acid obtained is converted into terephthalic acid by the Raecke (Henkel) rearrangement reaction, which can be carried out using a salt catalyst, which in the present invention can comprise cobalt magnesium salt.

According to the Henkel rearrangement reaction, a salt of the source material acid is formed from the source material acid and the salt catalyst, which thereafter is heated to a temperature of at least 300° C., and particularly 330-500° C., and more particularly 350-450° C., most suitably in an inert gas atmosphere. As a result, the salt of terephthalic acid is obtained.

Regarding the conversion of p-cymene into terephthalic acid, a reference is made to the publication Senseman, C. E., Stubbs, J. J., Ind. Eng. Chem., 1931, 23 (10), p. 1129.

When so desired, the obtained terephthalic acid can be esterified using any alcohol suitable for the purpose, such as methanol, and the dimethyl or corresponding terephthalate obtained as a result of the reaction of which can be polymerized into a desired polyester in a well-known manner.

Correspondingly, from the bio-based terephthalic acid produced according to the invention, bio-based polyesters, such as polyethylene terephthalate and polybutylene terephthalate, can be manufactured by polymerizing it with a bio-based diol.

Either these bio-based monomers can be used to increase the bio monomer portion of the polymer, or only the bio-based monomers manufactured according to the above can be used for the polymerization.

BRIEF DESCRIPTION OF THE DRAWINGS

In the following, the invention is described in more detail, first, with reference to the appended drawing:

FIG. 1 schematically presents equipment that is intended for the application of the invention.

DETAILED DESCRIPTION OF THE DRAWING

The basic stages of the hydrodeoxygenation and cracking processes of the fatty and resin acids of the bio oil, such as tall oil, according to the drawing, are the catalytic deoxygenation and cracking stages 2, 3 that take place in a vertical reactor 1, and the further processing of the liquid hydrocarbons obtained from these stages in separate equipment 4 that corresponds to the technology known as such in the field of petrochemistry. The feeding 5 of tall oil fatty acids, which are separated by distillation and which can include, for example, 25% of resin acids, is carried out to the upper end of the reactor 1. In addition, hydrogen can be brought to the upper end of the reactor 1 from a line 6. The reactor 1 is filled with quartz wool that works as bed material 7, its superimposed zones 2, 3, which are apart from each other, having a NiMo catalyst to deoxygenate the acids that are fed and zeolite or montmorillonite catalyst to crack the carbon chains. The flow direction of the liquid and gas phases in the reactor 1 is from top to bottom. To adjust the reaction temperatures, the reactor 1 is provided with an electric heater 8.

The hot reaction products that exit through the lower end of the reactor 1 are conducted to a cooler 9, and the liquefied product moves through a line 10 to a separating tank 11, which separates the aqueous phase 12 from the oil phase 13. The oil phase 13, the main component of which typically consists of saturated aliphatic hydrocarbons and which can also contain variable amounts of cyclic and aromatic hydrocarbons, unsaturated hydrocarbons and fatty alcohols, moves to further processing 4, where aromates A are recovered and further processed by the processes according to prior art and where low-molecular olefins 14 are obtained by steam cracking. The olefins can be used as the source material for the manufacture of bio polymers, such as polyethylene or polypropylene. The monoaromates that are to be converted into terephthalic acid are separated from the aromates.

The gas, which is not condensed in the cooler 9 and which contains hydrogen, oxides of carbon, possible low-molecular hydrocarbons and other impurities, moves to a purifier 15, which separates hydrogen from the other gas components. Pure hydrogen is circulated through the line 16 back to the upper end of the reactor 1 so as to constitute the deoxygenation gas, and the oxides of carbon and other impurities 17 are removed from the process.

An alternative implementation to the process according to the invention is that the zeolite catalyst 3 in the reactor 1 is replaced with a montmorillonite catalyst. In other respects, the equipment and the process flow are according to the drawing.

Example 1

Example tests 1-6, which comprise hydrodeoxygenation (HDO) and/or catalytic cracking (CC), were carried out on a batch principle as a flow through the reactor without circulating the gas phase. The ranges of fluctuation mentioned hereafter refer to differences between the tests in the parameters. The liquid and gas phases obtained from the reactor were analyzed. In the process according to the invention, the subsequent steam cracking of the organic liquid phase was not carried out, because it is technology that is well-known by those skilled in the art and, on the basis of the analyses, the applicability of the liquid to steam cracking was obvious.

A zeolite catalyst (ZSM-5) and its nickel molybdenum catalyst (NiMo, with aluminum oxide), a montmorillonite catalyst or a combination thereof were packed in the vertical reactor tube inside the electric furnace. The amount of each catalyst in grams is shown in table 1. The NiMo catalyst was pre-sulfudized by conducting a hydrogen sulfide-bearing hydrogen flow through the reactor pipe that was packed with the catalysts, at a temperature of 393° C. for five hours.

Depending on the test, the temperature of the reactor tube was adjusted to 360-450° C. and hydrogen gas was conducted through it at a pressure of 31-32 bars from top to bottom. The hydrogen flow in the reactor was set at about 1 g/h; the fluctuation range was 0.87-1.40 g/h. When the flow and temperatures had become steady, pumping of tall-oil distillate into the reactor pipe was started in addition to hydrogen, containing a few resin acids in addition to free fatty acids. There was also an unsaponifiable fraction among them. The acid value fluctuated from the lowest 174 to <200. Feeding of the tall-oil distillate into the reactor pipe took place from above, downstream with the hydrogen flow. The feeding velocity of the tall-oil distillate was set at 6.0-8.3 g/h. Regarding the catalysts, the WHSV (weight hourly space velocity) thus fluctuated within 2.0-2.3 $h^{-1}$ for the HDO catalyst, and 2.0-6.0 $h^{-1}$ for the CC catalyst, respectively.

The liquid/gas flow coming out from the lower end of the reactor was conducted into a pressurized collector tray that was cooled with cold water. The entire liquid contents of the collector tray were recovered at one hour intervals. The gas flow exiting the collector tray was conducted into the atmospheric air through a decompression valve. The composition of the gas flow was measured by an on-line analyzer at one-hour intervals, and the reactor was run for a total of 10 hours.

At the running time of eight hours, when the reactor was completely balanced, a minimum of 83% of the liquid product from the amount of tall-oil distillate that was fed were recovered. The liquid product comprised an organic phase and some separated water. The total amount of hydrocarbons in the liquid product fluctuated within 50-73% of the amount of organic phase, being at its lowest in the DTO feed with the NiMo/ZSM-5 catalyst and, at its highest, in the TOFA feed with the NiMo catalyst. The approximate compositions of the organic phase fluctuated considerably and they are shown in table 1 for the following components: aromatic hydrocarbons, saturated hydrocarbons, unsaturated, aliphatic hydrocarbons, and fatty alcohols in all, and cyclic hydrocarbons. Depending on the test, the gas flow exiting the reactor contained 2-17% of reaction products from the amount of tall-oil distillate fed; the lowest gas yield coming, at its highest, for the TOFA feed with the NiMo catalyst, and the highest one for the DTO feed with the NiMo/ZSM-5 catalyst. The reaction products of the gas flow were: carbon monoxide, carbon dioxide, a total of C1 and C2 hydrocarbons, a total of C3 hydrocarbons, C4 hydrocarbons, and heavier hydrocarbons in proportions that can be read from the table 1.

The mass balance measured in the test closed fairly well. The measured mass flows coming out totaled in at least 84%; at the most, 97% for the DTO feed with the NiMo/ZSM-5 composite catalyst, of all the flows that were fed into the reactor.

The results of tests 1-6 are in the following table. The feed of tests 1, 3, and 5 comprised a fatty acid fraction distilled from tall oil (TOFA), containing about 2% of resin acids; that of test 4 was distilled tall oil (CTO), where the amount of resin acids was about 25-30%; and that of tests 2 and 6 was crude tall oil (CTO), where the amount of resin acids was about 25%. The tests 1-3 and 5 were according to the invention, the tests 4 and 6 were reference tests.

The catalysts are shown separately for the hydrodeoxygenation stage (HDO) and the catalytic cracking stage (CC).

In test 4, which comprised the CC stage only, the lack of saturated hydrocarbons indicates an excessive advance of cracking and, thus, the importance of the HDO stage. Tests 5 and 6 indicate that the resin acids of the source material increase the portion of aromates; in test 6, to an unfavorably high level.

TABLE 1

| | sample | | | | | |
|---|---|---|---|---|---|---|
| Test | 1 | 2 | 3 | 4 | 5 | 6 |
| Hours from starting the run, h | 9 | 9 | 8 | 8 | 5 | 6 |
| Feed | TOFA | CTO | TOFA | DTO | TOFA | CTO |
| g/h | 7.0 | 6.4 | 8.3 | 6.0 | 6.4 | 6.0 |
| Fatty acids | 91.0 | 50.0 | 91.0 | 70.0 | 91.0 | 50.0 |
| Resin acids | 2.0 | 25.0 | 2.0 | 27.5 | 2.0 | 25.0 |
| Unsaponifiable | 7.0 | 25.0 | 7.0 | 2.5 | 7.0 | 25.0 |
| Acid value | 174 | <200 | 174 | 190 | 174 | <200 |
| Catalyst, g | NiMo 3 | NiMo 3 | NiMo 3 ZSM-5 1 | NiMo 3 ZSM-5 1 | NiMo 3 Montm 3 | NiMo 3 Montm 3 |
| Temperature, C. | 363 | 360 | 369 | 368 | 450 | 450 |
| Pressure, bar | 32 | 31 | 33 | 32 | 99 | 104 |
| WHSV for the HDO catalyst, 1/h | 2.3 | 2.1 | 2.0 | 2.0 | 2.1 | 2.0 |
| WHSV for the CC catalyst, 1/h | | | 5.8 | 6.0 | 2.1 | 2.0 |

TABLE 1-continued

|  | sample | | | | | |
|---|---|---|---|---|---|---|
| Test | 1 | 2 | 3 | 4 | 5 | 6 |
| Hydrogen feed into the reactor, g/h | 1.40 | 1.30 | 0.87 | 1.00 | 1.40 | 1.40 |
| Hydrogen/Feed, w/w | 0.20 | 0.20 | 0.15 | 0.16 | 0.21 | 0.2 |
| Liquid product | | | | | | |
| Approximate yield, % of liquid feed | 99 | 85 | 83 | 84 | 92 | 85 |
| Composition, % of organic phase: | | | | | | |
| Aromates | 4 | 29 | 6 | 22 | 10 | 25 |
| containing polycyclic | | | | | 3 | 13 |
| Saturated | 62 | 24 | 42 | 18 | 36 | 27 |
| Unsaturated aliphatic/fatty alcohols | 5 | 2 | 10 | 1 | 1 | 1 |
| Cyclic | 0 | 7 | 3 | 8 | 7 | 6 |
| Hydrocarbons in all, % from organic phase | 73 | 60 | 61 | 50 | 56 | 59 |
| Water content of liquid product, % | | | | | 14.3-11.1 | 1.5-6.8 |
| Gas product | | | | | | |
| Approximate yield, % from the feed | 2 | 5 | 10 | 17 | 6 | 10 |
| Composition, % from gaseous reaction products: | | | | | | |
| CO | 0 | 34 | 16 | 12 | 10 | 10 |
| CO2 | 43 | 45 | 23 | 20 | 9 | 6 |
| C1 + C2 | 8 | 10 | 2 | 3 | 41 | 42 |
| C3 | 0 | 3 | 21 | 29 | 23 | 28 |
| C4 | 0 | 0 | 28 | 28 | 13 | 9 |
| C5 | 0 | 3 | 8 | 6 | 4 | 3 |
| C6 | 0 | 0 | 1 | 0 | 1 | 1 |
| AcH | 0 | 0 | 2 | 1 | | 1 |
| Measured hydrogen flow out, g/h | 1.01 | 0.81 | 0.65 | 0.69 | 0.82 | 0.99 |
| Mass balance Flow rates out, % of all the feed | 96 | 84 | 92 | 97 | 93 | 92 |
| Carbon content of catalysts after the run, % | | | | | 8 h | 10 h |
| NiMo | | | | | 7.8 | 7.4 |
| Montmorillonite | | | | | 2.5 | 3.3 |

Example 2

Tall oil containing about 30% of resin acids, about 65% of fatty acids, and 5% off neutral ingredients, was conducted as a continuous flow into a reactor, the catalyst bed of which contained a NiMo/y-Al$_2$O$_3$ catalyst, which had been pre-sulfurized with sulfur compounds and stabilized with hydrogen thereafter. The feed of tall oil into the reactor was 1.45 kg/h and the WHSV was 2.1 h$^{-1}$. The tall oil was reacted with hydrogen in the catalyst bed at a temperature of 353.4° C. and a pressure of 49.5 bars, whereby the conversion of hydrogen was 18 mol-percent.

After continuing the reaction under stable conditions for 18 hours, a yellow liquid reaction product was recovered during 3 hours, containing 29% of aromates in all and 16% of monoaromates, in particular. Xylene isomers could be separated from the yield by distillation and converted into terephthalic acid by means of well-known methods.

The invention claimed is:

1. A method of manufacturing aromatic hydrocarbons from a tall oil-based raw material, the method comprising:
   feeding, into a fixed catalyst bed, hydrogen gas and a bio oil, which consists of 2-90% of tall oil fatty acids, 2-98% of tall oil resin acids and, optionally, other vegetable oils;
   catalytically deoxygenating the bio oil in the bed with hydrogen;
   cooling the flow exiting the bed, and dividing the flow into a hydrocarbon-bearing liquid phase and a gas phase; and
   recovering one or more aromatic hydrocarbons selected from a group comprising o-xylene, m-xylene, p-xylene and a cymene from the hydrocarbon-bearing liquid phase,
   wherein a deoxygenation catalyst and a cracking catalyst are used, which are different from each other and located sequentially apart from each other in the catalyst bed that is formed by a solid bed material.

2. The method according to claim 1, wherein the bio oil contains at least 25% of tall oil resin acids.

3. The method according to claim 1, wherein the bio oil has been separated from crude tall oil by distillation.

4. The method according to claim 1, wherein the catalyst of the deoxygenation stage is a NiMo catalyst.

5. The method according to claim 1, wherein the catalyst of the cracking stage is acidic.

6. The method of claim 5, wherein the acidic catalyst comprises an acidic zeolite catalyst.

7. The method of claim 6, wherein the acidic zeolite catalyst comprises a ZSM-5 catalyst.

8. The method according to claim 1, wherein oxygen compounds are removed from the raw material by use of hydrogen and the said deoxygenation or cracking catalyst or a combination thereof at 330-450° C. and a pressure of 50-100 bars.

9. The method according to claim 1, wherein the flows in the catalyst bed take place from top to bottom.

10. The method according to claim 1, wherein water is separated from the liquid phase of the reaction yield before further processing the hydrocarbon-bearing liquid.

11. The method according to claim 1, wherein one or more aromatic hydrocarbons are separated from the reaction yield by distillation.

12. The method according to claim 1, further comprising:
separating an aromatic hydrocarbon selected from a group comprising o-xylene, m-xylene, p-xylene and a cymene from the liquid phase; and
subjecting the separated hydrocarbon to oxygenation and a possible rearrangement reaction, so that terephthalic acid is obtained as the end product.

13. The method according to claim 12, wherein oxygenation of the separated hydrocarbon is carried out with a chemical or biochemical oxidizer.

14. The method according to claim 13, wherein the chemical or biochemical oxidizer comprises chromic acid.

15. The method according to claim 12, wherein p-xylene is separated from the liquid phase and oxidized into terephthalic acid.

16. The method according to claim 12, wherein o-xylene is separated from the liquid phase and oxidized into phthalic acid, which thereafter is converted by means of the Raecke or Henkel rearrangement reaction into terephthalic acid using a salt catalyst.

17. The method according to claim 16, wherein the salt catalyst comprises a cobalt-magnesium salt.

18. The method according to claim 12, wherein in the rearrangement reaction, the reaction mixture is heated to a temperature of at least 300° C. in an inert gas atmosphere.

19. The method according to claim 18, wherein the reaction mixture is heated to a temperature of 330-500° C.

* * * * *